United States Patent
Bar-Tal et al.

(10) Patent No.: US 10,973,588 B2
(45) Date of Patent: Apr. 13, 2021

(54) ON-THE-FLY CALIBRATION FOR CATHETER LOCATION AND ORIENTATION

(71) Applicant: Biosense Webster (Israel) Ltd., Yokneam (IL)

(72) Inventors: Meir Bar-Tal, Haifa (IL); Ran Peled, M.P. Misgav (IL); Fares Safe, Yanuh (IL); David Izraeli, Haifa (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 286 days.

(21) Appl. No.: 16/169,524

(22) Filed: Oct. 24, 2018

(65) Prior Publication Data

US 2020/0129238 A1    Apr. 30, 2020

(51) Int. Cl.
| | |
|---|---|
| G01V 3/08 | (2006.01) |
| A61B 17/00 | (2006.01) |
| A61B 34/20 | (2016.01) |
| A61B 5/06 | (2006.01) |

(52) U.S. Cl.
CPC ............. *A61B 34/20* (2016.02); *A61B 5/062* (2013.01); *G01V 3/081* (2013.01); *A61B 2017/00725* (2013.01); *A61B 2034/2051* (2016.02); *A61B 2034/2072* (2016.02)

(58) Field of Classification Search
None
See application file for complete search history.

(56) References Cited

U.S. PATENT DOCUMENTS

| | | | |
|---|---|---|---|
| 5,391,199 A | 2/1995 | Ben-Haim | |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,633,773 B1 * | 10/2003 | Reisfeld | A61B 5/06 382/128 |
| 6,690,963 B2 | 2/2004 | Ben-Haim et al. | |
| 7,835,879 B2 | 11/2010 | Vocali et al. | |

(Continued)

FOREIGN PATENT DOCUMENTS

| | | |
|---|---|---|
| EP | 1502545 A1 | 2/2005 |
| WO | WO 96/05768 A1 | 2/1996 |
| WO | 0068637 A1 | 11/2000 |

OTHER PUBLICATIONS

Electromagnetic tracking and steering for catheter navigation, 2014, University College Cork. p. 175-180 (Year: 2014).*

(Continued)

*Primary Examiner* — Roy Y Yi

(74) *Attorney, Agent, or Firm* — Notaro, Michalos & Zaccaria P.C.

(57) ABSTRACT

A method includes retrieving from a memory a stored sensitivity table that associates magnetic position sensor readings with measured magnetic fields. One or more calibration values for the magnetic position sensor are estimated during a catheterization procedure in which a magnetic position sensor, fitted at a distal end of a catheter, is placed in an organ of a patient, based on (i) the stored sensitivity table and (ii) readings acquired by the magnetic position sensor while in the organ. Based on the one or more calibration values, a location of the distal end in the organ is magnetically tracked.

14 Claims, 2 Drawing Sheets

(56) References Cited

U.S. PATENT DOCUMENTS

| | | |
|---|---|---|
| 8,082,020 B2 | 12/2011 | Bar-Tal et al. |
| 8,577,637 B2 | 11/2013 | Vogt |
| 8,818,747 B2 | 8/2014 | Weiss et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2020/0037923 A1* | 2/2020 | Lu ................. A61B 5/0035 |

OTHER PUBLICATIONS

Chao Hu et al: "The Calibration of 3-Axis Magnetic Sensor Array System for Tracking Wireless Capsule Endoscope", Intelligent Robots and Systems, 2006 IEEE/RSJ International Conference on, IEEE, PI, Oct. 1, 2006 (Oct. 1, 2006), pp. 162-167.

Popek Katie Met Al: "Six-Degree-of-Freedom Localization of an Untethered Magnetic Capsule Using a Single Rotating Magnetic Dipole", IEEE Robotics and Automation Letters, IEEE, vol. 2, No. 1, Jan. 1, 2017 (Jan. 1, 2017), pp. 305-312.

Extended European search report for corresponding European application No. EP 19204802.3, dated Mar. 13, 2020.

\* cited by examiner

ON-THE-FLY CALIBRATION FOR CATHETER LOCATION AND ORIENTATION

FIELD OF THE INVENTION

The present invention relates generally to the calibration of medical probes, and particularly to calibration of magnetic catheter-based location and orientation tracking systems.

BACKGROUND OF THE INVENTION

Various methods were proposed for the calibration of magnetic sensors. For example, in another field, U.S. Pat. No. 8,577,637 describes a system and method of determining a magnetic field and magnetic compass calibration. One embodiment is a method of determining a magnetic field vector. The method comprises storing, for each of a plurality of sensor orientations, one or more calibration components. Then, determining, for a sensor orientation not included in the plurality of sensor orientations, a magnetic field vector and a gravity vector. Then, iteratively estimating one or more calibration coefficients based on the stored components, estimating the determined magnetic field vector, and estimating the determined gravity vector, wherein the calibration coefficients are updated during each of a plurality of iterations. Finally, determining a sensor-orientation-independent magnetic field vector based on at least one of the calibration coefficients.

As another example, U.S. Pat. No. 8,818,747 describes a method for calibrating a triaxial magnetic field sensor that includes steps for determining an offset of recorded measured values of the magnetic field sensor using a superposed signal and for determining the sensitivity of the magnetic field sensor along the first measuring axes. The determination of the sensitivity includes steps for determining the sensitivity of the magnetic field sensor along a first measuring axis and for determining the sensitivity of the magnetic field sensor along the other measuring axes based on the sensitivity of the first measuring axis and the determined offset.

U.S. Pat. No. 8,082,020 describes a method for tracking a position of an object that includes using a field sensor associated with the object to measure field strengths of magnetic fields generated by two or more field generators, wherein a measurement of at least one of the field strengths is subject to a distortion. Rotation-invariant location coordinates of the object are calculated responsively to the measured field strengths. Corrected location coordinates of the object are determined by applying to the rotation-invariant location coordinates a coordinate correcting function so as to adjust a relative contribution of each of the measured field strengths to the corrected location coordinates responsively to the distortion in the measured field strengths.

In another field, U.S. Pat. No. 7,835,879 describes measurements that are acquired from a magnetic sensor during a non-pre-ordered movement, and a plurality of sets of solutions that are determined for respective expected values of intensity of the Earth's magnetic field. The solutions are defined by a plurality of parameters, including at least one gain value for each detection axis of the magnetic sensor. For each solution, a figure of merit is determined, correlated to a calibration error, and a partial solution is selected in each set of solutions, based on the figure of merit. Once a gain confidence interval has been defined, a calibration solution is selected based on the figure of merit, from among the partial solutions having respective gain values all falling within the gain confidence interval.

SUMMARY OF THE INVENTION

An embodiment of the present invention provides a method including retrieving from a memory a stored sensitivity table that associates magnetic position sensor readings with measured magnetic fields. One or more calibration values for the magnetic position sensor are estimated during a catheterization procedure in which a magnetic position sensor, fitted at a distal end of a catheter, is placed in an organ of a patient, based on (i) the stored sensitivity table and (ii) readings acquired by the magnetic position sensor while in the organ. Based on the one or more calibration values, a location of the distal end in the organ is magnetically tracked.

In some embodiments, the method further includes storing in the memory the one or more estimated calibration values.

In some embodiments, estimating the one or more calibration values includes minimizing a cost-function to obtain equations that associate the sensor readings with the measured magnetic fields.

In an embodiment, tracking the location includes solving the obtained equations to track the location and orientation of the distal end in the organ.

There is additionally provided, in accordance with an embodiment of the present invention, a system including a memory and a processor. The memory is configured to store a sensitivity table that that associates magnetic position sensor readings with measured magnetic fields. The processor is configured to retrieve the stored sensitivity table from the memory, and, during a catheterization procedure in which a magnetic position sensor, fitted at a distal end of a catheter, is placed in an organ of a patient, estimate one or more calibration values for the magnetic position sensor based on (i) the stored sensitivity table and (ii) readings acquired by the magnetic position sensor while in the organ. The processor is further configured to, based on the one or more calibration values, magnetically track a location of the distal end in the organ.

The present invention will be more fully understood from the following detailed description of the embodiments thereof, taken together with the drawings in which:

DETAILED DESCRIPTION OF EMBODIMENTS

Overview

Figure 1:
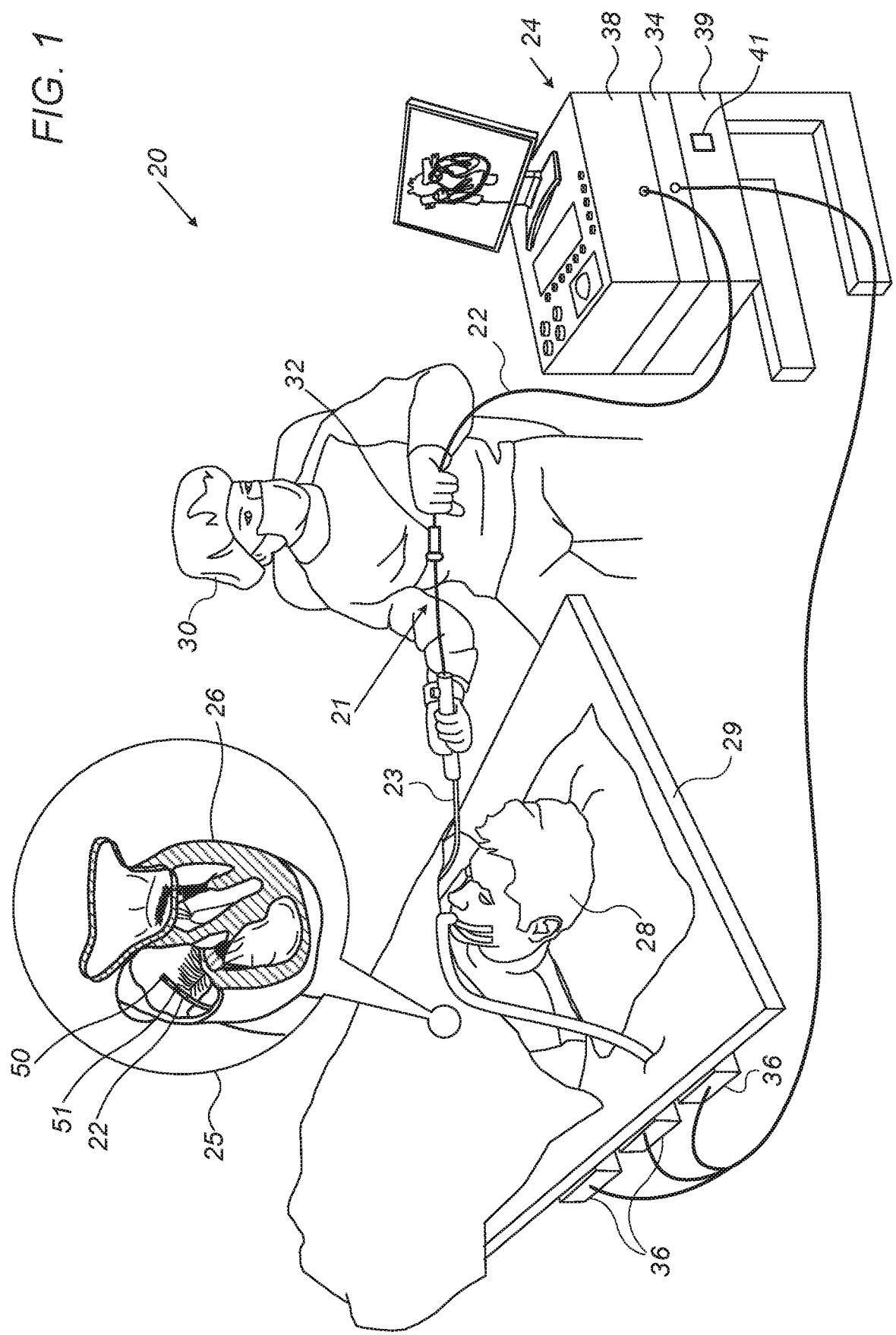
FIG. 1 is a schematic, pictorial illustration of a catheter-based magnetic location and orientation tracking and ablation system, in accordance with an embodiment of the present invention.

The location and orientation (L&O) of a distal end of a catheter can be magnetically tracked in an organ of a patient using a magnetic catheter-based system that tracks the L&O of a magnetic sensor included in the catheter distal end. Before the catheter can be used in such a way with a patient, the sensor should be fully calibrated, e.g., in the factory. The calibration process typically involves establishing relations between voltage readings from sensor elements, such as coils, taken in the presence of known magnetic fields, with a known orientation of the distal end. The resulting relations, e.g., a calibration function named hereinafter a "sensitivity factor" of the sensor, is stored in a memory and supplied with the catheter and is catheter-specific.

In some embodiments, a magnetic position sensor comprises either a single coil (M=1), or two orthogonal coils (M=2), or three mutually orthogonal coils (M=3). In general, mutual orthogonality of coils is not mandatory, but coils should be set such that they span a plane (using two coils) or a volume (using three sensors). Using the one or more M coils, the sensor measures M different voltages that are each modulated at a distinct carrier frequency that encodes a spatial axis in real space, as described below. As there are six unknowns, i.e., location and orientation coordinates, x,y,z, $\alpha,\beta,\gamma$, the last three corresponding to azimuth, elevation & roll angles of a coil, a sensitivity factor of a magnetic position sensor may be written as a 3×3 matrix having six independent parameters, as described below.

For its calibration, each catheter may be individually placed in a magnetic calibration apparatus in the factory, voltages of the sensor coils read, and the read voltages used to calculate the sensitivity factor for the sensor. The sensor sensitivity factor enables voltage readings acquired during a medical procedure to be converted to magnetic field values. Then, the magnetic field values are converted, for example, by using a known model of the magnetic field, to spatial coordinates that describe a location and orientation of the distal end in the organ. An example of a catheter-based position tracking system applying the above method is the Carto®3 system (made by Biosense-Webster, Irvine, Calif.). The calibration process described above, however, is time-consuming and costly, which may limit mass production of catheters with such calibration requirements.

Embodiments of the present invention that are described hereinafter provide techniques to calibrate a magnetic sensor after the catheter is inserted into an organ of a patient. The disclosed calibration, performed, for example, at a beginning of a catheterization procedure, eliminates the need for individual factory calibration of each catheter. In some embodiments, a processor estimates one or more calibration values for the magnetic position sensor based on (i) the stored sensitivity factor (e.g., a sensitivity table) and (ii) readings acquired by the magnetic position sensor while in the organ.

To enable the calibration, embodiments of the disclosed method use an initial, coarse, "factory" calibration that provides an approximate value of the sensitivity factor. This calibration, which need not be performed more than once, yields an approximate value of the sensitivity factor that is valid for all sensors of the same type (i.e., the initial calibration yields an approximate, "average" sensitivity factor, which was defined during the catheter development phase, i.e., off-line the production phase).

For finalizing the calibration, the disclosed method utilizes a large redundancy in magnetic measurements during catheterization. For example, a magnetic location pad generator of magnetic fields of a catheter-based location and orientation CARTO® system, which is equipped with three sets of tri-axial magnetic-field generators, generates nine voltages at a single axis sensor (SAS), eighteen voltages at a double axis sensor (DAS), and twenty-seven voltages at a three axial sensor (TAS), whereas there are only six unknowns for the sensitivity factor matrix in addition to the six unknowns of the location and orientation of the catheter.

Thus, in some embodiments, at the very beginning of a catheterization procedure, a processor runs an L&O calibration process which uses the above noted redundancy in magnetic measurements to iteratively correct the approximate "average" sensitivity factor. In this way, the processor effectively generates an exact expression for the sensitivity factor, so that sensor readings may be accurately converted to spatial coordinates. Since sensor readings are typically taken at the rate of tens of Hertz, it typically takes less than a second for the processor to run the L&O calibration process and generate the correct location and orientation readings of the distal end.

The disclosed L&O calibration method enables efficient mass production, and shipping to numerous users, of catheters that are universally initially calibrated (e.g., factory partially calibrated), the complete calibration of which can be completed, on-site, in a process that takes less than a second at the beginning of a catheterization procedure. The disclosed method also eliminates the need for supplying each catheter together with its individual calibration results. Complications that are avoided by the disclosed method are, for example, a reduced risk from error in the position and orientation of a catheter during a clinical procedure. Furthermore, the disclosed technique saves an inclusion of a small nonvolatile memory in the catheter and configuration of the tracking system to read the catheter calibration results from it on initialization.

System Description

FIG. 1 is a schematic, pictorial illustration of a catheter-based magnetic location and orientation tracking and ablation system 20, in accordance with an embodiment of the present invention. System 20 comprises a catheter 21, having a shaft distal end 22 (shown in inset 25) that is navigated by a physician 30 into a heart 26 of a patient 28 via the vascular system. In the pictured example, physician 30 inserts shaft distal end 22 through a sheath 23, while manipulating the distal end of shaft distal end 22 using a manipulator 32 near the proximal end of the catheter. As shown in inset 25, a magnetic sensor 51 having M coils (i.e., an M-axis sensor, with M=1, or M=2, or M=3) is contained within shaft distal end 22, as well as an ablation tip 50.

In the embodiments described herein, catheter 21 is used for ablation of tissue in heart 26. Although the pictured embodiment relates specifically to the use of ablation tip 50 for ablation of heart tissue, the elements of system 20 and the methods described herein may alternatively be applied in position tracking of other types of catheters, such as of ultrasound catheters and electrophysiological mapping catheters (e.g., LASSO® position tracking catheters or PENTARAY® mapping catheters, both made by Biosense-Webster Inc.).

The proximal end of catheter 21 is connected to a control console 24. Console 24 comprises a processor 39, typically a general-purpose computer, with suitable front end and interface circuits 38 for receiving signals from catheter 21, as well as for applying energy via catheter 21 to ablate tissue in heart 26 and for controlling the other components of system 20. Console 24 comprises a memory 41 that stores the sensitivity factors that processor 39 calculated during the L&O calibration process. Console 24 also comprises a driver circuit 34, configured to drive magnetic field generators 36.

In some embodiments, system 20 includes three magnetic field generators 36, each generator comprises three magnetic field transmitters (i.e., total of K=9 transmitters). In general, there are a total of K transmitters (K being an integer) that induce K modulated voltages for each axis of a magnetic sensor (i.e., K voltages for a SAS, 2K voltages for a DAS, and 3K voltages for a TAS).

During a navigation of shaft distal end 22 in heart 26, console 24 receives signals from magnetic sensor 51 in response to magnetic fields from external field generators 36 of a location pad, for example, for the purpose of measuring a location and orientation of ablation tip 50 in the heart and, optionally, presenting the tracked position on a display 27. Magnetic field generators 36 are placed at a position external to patient 28, e.g., below a patient table 29. These position signals are indicative of the location and orientation of ablation tip 50 in the coordinate system of the position tracking system.

This method of position sensing using external magnetic fields is implemented in various medical applications, for example, in the CARTO™ system, produced by Biosense-Webster Inc., and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 39 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

On-The-Fly Calibration Method for Catheter Location and Orientation

Figure 2:
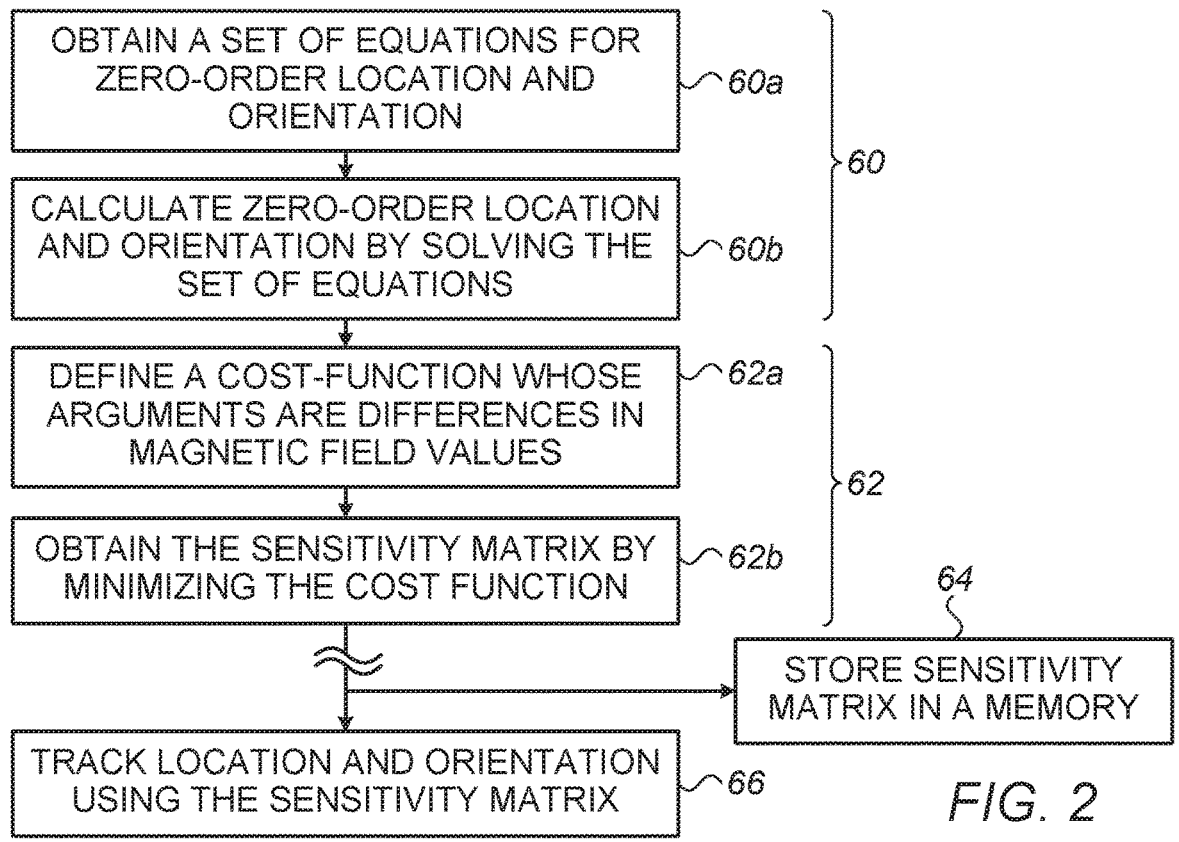
FIG. 2 is a flow chart of a Location and Orientation (L&O) calibration process, in accordance with an embodiment of the present invention.

FIG. 2 is a flow chart of a Location and Orientation (L&O) calibration process, in accordance with an embodiment of the present invention. The L&O calibration process may be applied by processor 39 of system 30 as distal end 22 is being inserted into heart 26.

Immediately after position-indicative measurements (e.g., voltage readings) are available from a M-coil magnetic sensor 51, processor 39 runs the L&O calibration process for initially finding an approximate location and orientation $q_0=(x_0,y_0,z_0,\alpha_0,\beta_0,\gamma_0)$ of sensor 51, at a zero-order location step 60.

The calculation of $r_0=(x_0,y_0,z_0)$ is based on the known 3×3 factory sensitivity matrix (i.e., factory sensitivity factor), $S_0$, and on the voltages (provided herein by K×M matrix V) measured by the M coils of sensor 51, as explained in the patents incorporated by reference above.

In addition, the following inputs are known while applying the L&O calibration process:
1. A set of voltage measurements from a magnetic sensor at N different intra-cardiac locations ($r_i=[x_i,y_i,z_i]$; i=1 . . . N) and orientation ($o_i=[\alpha_i,\beta_i,\gamma_i]$, corresponds to azimuth, elevation & roll angles). The sensor comprises of M magnetic coils (as noted above, typically M is either 1, 2 or 3). Therefore, the voltages measured at a location $r_i$ are given by a vector $V_{ij}=[V_1, V_2, \ldots, V_M]_{ij}^T$ for each transmitter j. With K the number of transmitters such as j=1, . . . , K.

2. A magnetic field model $B_j(r_i)$ at each location i from each transmitter j. With K the number of transmitters such as j=1, . . . , K.

To find an approximate (i.e., zero-order) location and orientation $q_0$ of sensor 51, processor 39 runs the disclosed L&O calculation sub-steps comprising:

A sub-step 60a: deriving an equation for a zero-order location and orientation $q_0$; and A sub-step 60b: solving the equation to find the zero-order location and orientation $q_0$.

Sub-step 60a begins with noting that the coordinates of an interbody location to calculate, (x,y,z), are implicitly included in the matrix model of the magnetic field, $B_j(r_i)$, whereas the angles are included in a separate rotation matrix $R(o_i)$.

The relation between an estimated magnetic field matrix $\hat{B}$ and voltage matrix, V, at each estimated location $\hat{r}_i$ can thus be written given in general by matrix multiplication:

$$\hat{B}(\hat{r}_i)=R_i(\hat{o}_i)S(\hat{s})V_i \qquad \text{Eq. 1}$$

As seen, Eq. 1 connects the measured voltages with a spatial distribution of the magnetic fields that generate the voltages. $V_i$ is the voltage measurements taken at N unknown locations. Matrix $S(\hat{s})$ is the unknown sensor sensitivity matrix comprising elements $\hat{s}$ (i.e., calibration values $\hat{s}$). S is either symmetric, upper triangle or lower triangle (comprised of 6 unknowns). S matrix with 6 unknowns' vector $\hat{s}$ (subject to a predefine structure). In an embodiment, $S(\hat{s})$ is a conversion matrix from the sensor measured voltages to an orthonormal magnetic field in the coordinate system of system 20 (i.e., of generators 36).

$R_i(\hat{o}_i)$ is a rotation matrix that provides the orientation in the coordinate system of system 20 (i.e., of generators 36) of the sensor at an estimated location $\hat{r}$. Matrix R includes the three unknown rotation angles ($\alpha,\beta,\gamma$).

In total, there are twelve unknowns: six sensitivity elements of S (i.e., calibration values to estimate), three position coordinates x, y, and z, and three orientation angles $\alpha,\beta,\gamma$ in R.

A zero-order solution, $q_0$, is obtained by first deriving, from Eq. 1, a dipole location calculation comprising an inhomogeneous matrix equation for x,y,z,$\alpha,\beta,\gamma$:

$$R^T B=S(\hat{s}_0)V \qquad \text{Eq.2}$$

The derivation of Eq.2 is based on the orthogonality of the rotation matrix, R, (i.e., $R^T=R^{-1}$) and the available factory calibrated sensitivity factor $S(\hat{s}_0)$.

Eq. 2 represents a physical reality, and thus should have a unique valid solution. To obtain the solution, at sub-step 60b, the inhomogeneous system is triangulated, and the resulting equations are then solved. The calculation result is the approximate, zero order location, of the magnetic sensor, $q_0=(x_0,y_0,z_0,\alpha_0,\beta_0,\gamma_0)$.

Next, at calculation process 62, processor 39 calculates with the L&O calibration process, the required sensitivity matrix $S(\hat{s})$, which will be used in the clinical investigative session to track the location and orientation of sensor 51 magnetic. Process 62 begins with defining a cost-function, J, is at a cost-function construction step 62a:

$$J=\Sigma_{i=1}^N\Sigma_{m=1}^M\Sigma_{j=1}^K\|\mu B(\hat{r}_i)-R_i(\hat{o}_i)S(\hat{s})V_{i,j,m}\| \qquad \text{Eq. 3}$$

Cost function J represents the "distance," or norm, between the actual measured magnetic field and its estimation, $B(\hat{r}_i)-\hat{B}(\hat{r}_i)$ at each estimated location $\hat{r}_i$.

Next, processor 39 find the N×(3 locations+3 orientation)+6 (sensitivity) unknowns, $r_i, o_i, s$, that minimizes J:

$$\hat{r}_i, \hat{o}_i, \hat{s} = \underset{\hat{r}_i, \hat{o}_i, \hat{s}}{\operatorname{argmin}} \sum_{i=1}^{N} \sum_{m=1}^{M} \sum_{j=1}^{K} \|B(\hat{r}_i) - R_i(\hat{o}_i) S(\hat{s}) V_{i,j,m}\| \quad \text{Eq. 4}$$

Deriving that way ŝ (i.e., the 6 unknowns calibration values) is typically performed using library functions of a software such as MATLAB®, for example, using maximum-likelihood based solver or Monte Carlo based solver. The solution minimizes the norm ("distance") of the difference between the known magnetic field B($\hat{r}_i$) and the magnetic field estimation $\hat{B}(\hat{r}_i)$ at a set of N locations and N respective orientations is the best estimation of the above unknowns (in the sense of the above cost function).

As indicated by Eq. 4, the minimization of J yields a solution that, in addition to ŝ, includes a byproduct consisting of the N estimated locations $\hat{r}_i$ and N respective estimated orientations $\hat{o}_i$, of the catheter used during the L&O process. However, these initial values are typically not used for, for example, generating an anatomical map.

In some embodiments, the voltage readings required for running the L&O calibration process are received at a rate of 30 Hz. Thus, the L&O method fully calibrates a catheter in less than a second after the catheter is within the generator magnetic field working volume, pre the insertion into a heart of a patient. Henceforth, the position tracking system generates correct magnetic readings.

In an embodiment, in a storing in a memory step 64, processor 39 stores in memory 41 the sensitivity matrix S, that processor 39 calculated in step 62b (i.e., processor 39 stores in memory 41 the estimated calibration values). During a following clinical investigative session, system 20 uses the stored estimated calibration values to track a position and orientation of sensor 51, at a position and orientation tracking step 66.

The flow chart shown in FIG. 2 is chosen purely for the sake of conceptual clarity. FIG. 2 shows only part of the calculation steps, and the derivation of results, relevant to embodiments of the present invention. The cost function used in the calibration process may vary where other norm types are used.

Figure 3:
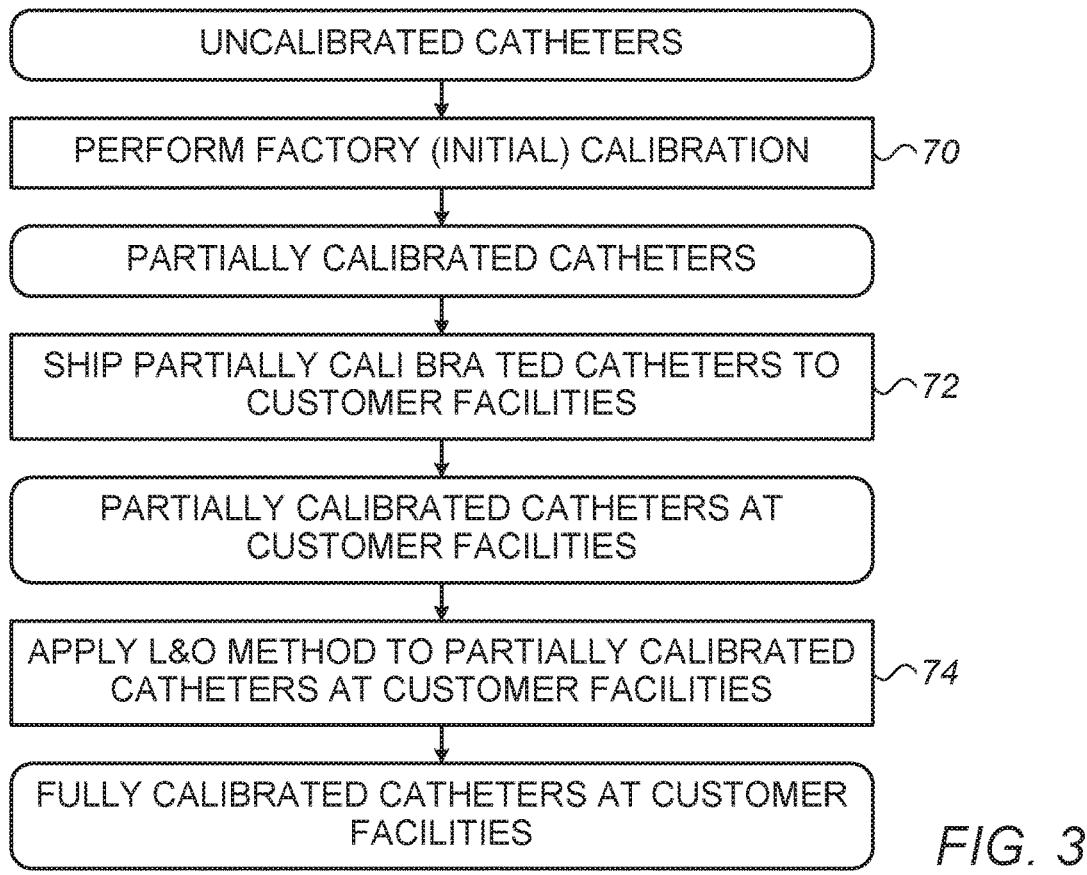
FIG. 3 is a flow chart that schematically illustrates a method for manufacturing catheters using the L&O calibration process illustrated in FIG. 2, in accordance with an embodiment of the present invention.

FIG. 3 is a flow chart that schematically illustrates a method for manufacturing catheters using the L&O calibration process illustrated in FIG. 2, in accordance with an embodiment of the present invention. A factory may manufacture hundreds of thousands of catheters, which are all universally (i.e., initially, or partially) factory calibrated, at a factory calibration step 70. These factory calibrated catheters are then shipped to numerous users, usually worldwide, at a shipment step 72. The partially calibrated catheters are substantially ready for use at customer facilities, in that a position tracking system that applies the L&O method fully calibrates the catheter at a very beginning of the catheterization procedure, i.e., over a period that typically lasts less than a second, and just before the catheter is inserted into a heart of a patient and system starts acquiring measurements, at an L&O calibration step 74.

Although the embodiments described herein mainly address cardiac applications, the methods and systems described herein can also be used in other applications, such as in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
retrieving from a memory a stored sensitivity table that associates magnetic position sensor readings with measured magnetic fields;
during a catheterization procedure in which a magnetic position sensor, fitted at a distal end of a catheter, is placed in an organ of a patient, estimating one or more calibration values for the magnetic position sensor based on (i) the stored sensitivity table and (ii) readings acquired by the magnetic position sensor while in the organ; and
based on the one or more calibration values, magnetically tracking a location of the distal end in the organ;
wherein the stored sensitivity table represents an initial coarse calibration associated with the magnetic position sensor.

2. The method according to claim 1, and comprising storing in the memory the one or more estimated calibration values.

3. The method according to claim 1, wherein estimating the one or more calibration values comprises minimizing a cost-function to obtain equations that associate the sensor readings with the measured magnetic fields.

4. The method according to claim 3, wherein tracking the location comprises solving the obtained equations to track the location and orientation of the distal end in the organ.

5. A system, comprising:
a memory, which is configured to store a sensitivity table that that associates magnetic position sensor readings with measured magnetic fields; and
a processor, which is configured to: retrieve the stored sensitivity table from the memory;
during a catheterization procedure in which a magnetic position sensor, fitted at a distal end of a catheter, is placed in an organ of a patient, estimate one or more calibration values for the magnetic position sensor based on (i) the stored sensitivity table and (ii) readings acquired by the magnetic position sensor while in the organ; and based on the one or more calibration values, magnetically track a location of the distal end in the organ;
wherein the stored sensitivity table represents an initial coarse calibration associated with the magnetic position sensor.

6. The system according to claim 5, wherein the processor is further configured to store in the memory the one or more estimated calibration values.

7. The system according to claim 5, wherein the processor is configured to estimate the one or more calibration values by minimizing a cost-function to obtain equations that associate the sensor readings with the measured magnetic fields.

8. The system according to claim 7, wherein the processor is configured to track the location by solving the obtained equations to track the location and orientation of the distal end in the organ.

9. The method according to claim 1, wherein the magnetic position sensor has a type, and the initial coarse calibration is valid for all sensors of the type.

10. The method according to claim 1, wherein the one or more calibration values for the magnetic position sensor includes an exact expression for the sensitivity factor that is a correction of the initial coarse calibration.

11. The method according to claim 10, wherein the exact expression is determined in less than one second.

12. The system according to claim 5, wherein the magnetic position sensor has a type, and the initial coarse calibration is valid for all sensors of the type.

13. The system according to claim 5, wherein the one or more calibration values for the magnetic position sensor includes an exact expression for the sensitivity factor that is a correction of the initial coarse calibration.

14. The system according to claim 13, wherein the exact expression is determined in less than one second.

\* \* \* \* \*